United States Patent [19]

Bovin et al.

[11] Patent Number: 5,571,836
[45] Date of Patent: Nov. 5, 1996

[54] VIRAL ATTACHMENT INHIBITORS

[76] Inventors: Nicolai V. Bovin, 117871, ul. Artsimovicha 11, 181 Moscow; Nargiz E. Bryamova, ul. Ostravitiyanova 16/4, 46 Moscow; Alexander B. Tuzikov, Ismaylowski, Prospekt 47, 4, Moscow; Mikhail N. Matrosovich, Ramenka Str., 9/2 Apt. 287; Larisa V. Mochalova, Ramenka ul. 9/3, 572, both of 117607 Moscow; Alexandra S. Gambaryan, ul. Vargy 40, 71, 117133 Moscow, all of Russian Federation

[21] Appl. No.: 438,661

[22] Filed: May 9, 1995

Related U.S. Application Data

[63] Continuation-in-part of PCT/US92/09745 Nov. 9, 1992.
[51] Int. Cl.$^6$ .................................................. A61K 31/35
[52] U.S. Cl. ................................................................. 514/459
[58] Field of Search ................................................. 514/459

[56] References Cited

PUBLICATIONS

Bovina et al 121 CA:149048w 1994.

*Primary Examiner*—Russell Travers
*Attorney, Agent, or Firm*—Hamilton, Brook, Smith & Reynolds, P.C.

[57] ABSTRACT

Viral attachment to target cells is inhibited by novel neuraminic acid compounds of the formula:

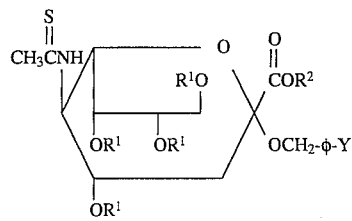

wherein $R^1$ is selected from the group consisting of hydrogen and acetyl; $R^2$ is selected from the group consisting of hydrogen and methyl; and Y is selected from the group consisting of:

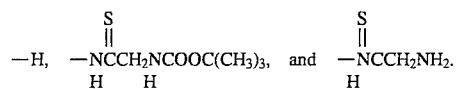

The novel compounds bind virus particles and are substantially uncleaved by neuraminidase. Coupling of the novel compounds to a polymer further inhibits viral attachment.

19 Claims, 1 Drawing Sheet

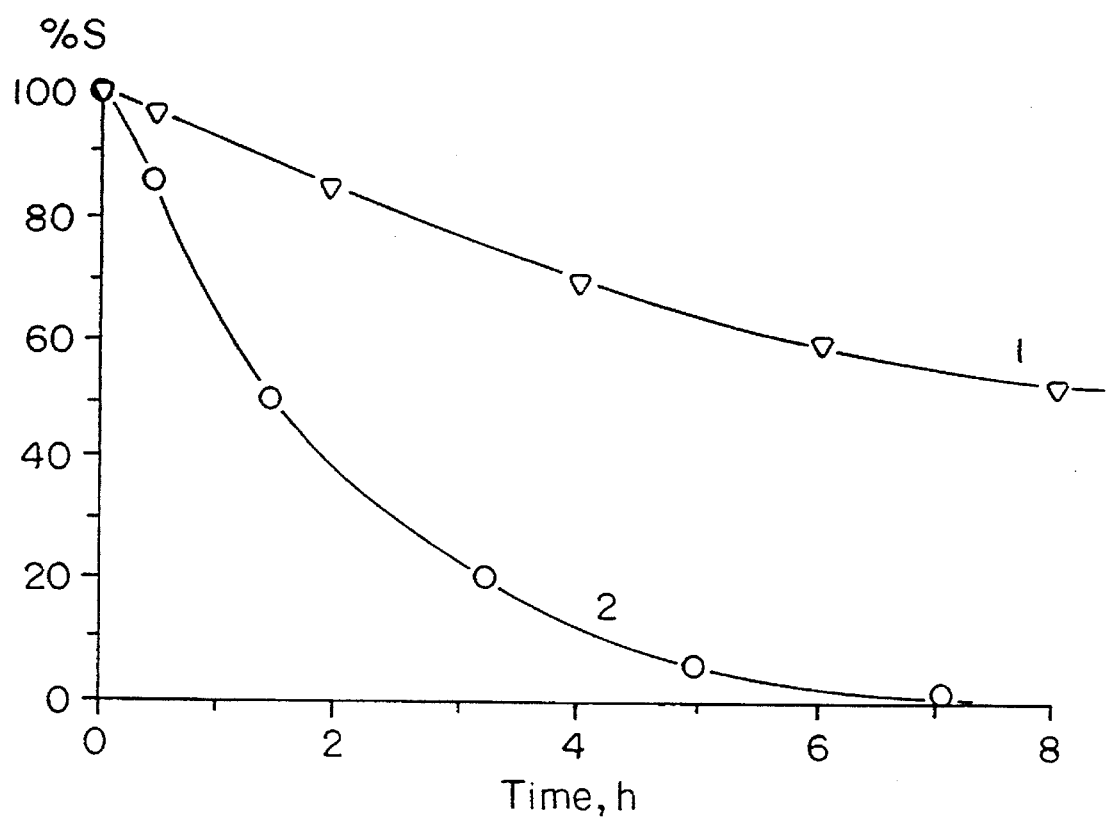

VIRAL ATTACHMENT INHIBITORS

RELATED APPLICATION

This application is a continuation-in-part of the U.S. designation of International Application No. PCT/US92/09745, filed on Nov. 9, 1992.

BACKGROUND OF THE INVENTION

Viral infections are a major cause of lost productivity among workers and can result in discomfort, illness, and even death. Some viruses are transmitted readily among individuals, with infections rates among local populations sometimes reaching sixty to eighty percent. Outbreaks of influenza virus infection in particular have reached epidemic and pandemic proportions.

Unlike the vast array of drugs available to treat bacterial infections, the number of agents effective in treating viral infections is quite limited. Because the viral life cycle is intimately involved with host cell metabolism, selective toxicity against viruses is difficult to achieve. Viruses that mutate readily into resistant strains limit the effectiveness of potential therapeutic agents.

The initial step in influenza virus infection is the attachment of the virus to various cell receptors. The ability to prevent attachment would provide a means by which viral infection could be prevented or its spread halted.

Attachment is mediated by the trimeric viral envelope glycoprotein hemagglutinin, which recognizes and binds sialic acid residues on host cell glycoproteins or glycolipids. Because sialic acid residues are found on a great many cell surface macromolecules, viral hemagglutinin binds a wide range of host cell receptors. A hemagglutinin receptor, therefore, is any host cell molecule containing a site that hemagglutinin will recognize and bind, with the major determinant for recognition being presence of a terminal sialic acid or neuraminic acid residue.

Competing with hemagglutinin for receptors is neuraminidase, a second viral envelope glycoprotein which binds and cleaves terminal sialic acid residues from host cell surface molecules. Cleavage of the terminal sialic acid residue by neuraminidase removes the site of hemagglutinin recognition and thereby prevents infection by the virus.

Hemagglutination and viral infection can be inhibited by soluble receptor analogs. These analogs can include the soluble portions of sialic acid-containing host cell surface macromolecules or even smaller portions thereof. Some low molecular mass sialic acid derivatives have been tested, but inhibitory activity is low. It has been shown that the α-benzyl glycoside of 5-acetyl neuraminic acid shows greater inhibition of attachment than 5-acetyl neuraminic acid itself. Inhibitory activity is decreased by neuraminidase cleavage of these receptor analogs, which effectively lowers the concentration of the analog with respect to hemagglutinin. The α-benzyl derivative of neuraminic acid is not immune to this cleavage.

Ideally, a viral attachment inhibitor should have the following properties:
1. The inhibitor should bind with hemagglutinin more tightly than with neuraminidase.
2. It should not be broken down or should be broken down only slowly by neuraminidase so that the analog will remain in the organism;
3. It should bind with the maximum possible number of virus strains.

Hemagglutinin recognizes sialic acids, a group of acidic sugars that includes N-acetyl neuraminic acid. Analogs of this compound have been synthesized. To be an effective attachment inhibitor, a synthetic analog should contain all of the elements of natural sialic acid that are required for hemagglutinin binding: a carboxyl group, a glycerol residue, and an acetamido group. Ideally, a virus attachment inhibitor should closely resemble the binding site of hemagglutinin, which exists on the surface of viruses as a trimer.

It has been known in the art that virus-cell interaction is multivalent and cooperative. Polyvalent receptor analogs, such as proteins conjugated with the sialic acid N-acetyl neuraminic acid, have been shown to be active in inhibiting hemagglutination. Attachment of sialic acids alone to a carrier does not afford resistance to neuraminidase cleavage, and as a result these multivalent receptor analogs would not be effective for extended prevention of viral infection.

The invention described herein relates to a synthetic analog of neuraminic acid that inhibits viral attachment and is resistant to cleavage by neuraminidase. The compounds described herein are useful in prophylaxis and early treatment of infection by multiple strains of influenza virus. Further, this synthetic analog being attached to a polymer yields a multivalent virus attachment inhibitor of increased inhibitory activity.

SUMMARY OF THE INVENTION

The invention relates to novel synthetic neuraminic acid compounds that inhibit viral attachment to target cells. Competition between the synthetic compounds and cell surface sialic acid residues for virus attachment sites effectively reduces the frequency, incidence, and severity of infection of the virus. Because the novel compounds resemble the target cell receptor and contain all the elements of natural neuraminic acid required for virus binding, inhibition of a wide range of virus strains can be achieved. In addition, resistance to neuraminidase cleavage improves the effective life of the novel compounds, allowing further reduction of the frequency, incidence, and severity of viral infection.

According to the invention, novel neuraminic acid derivatives having the general formula (I) are provided:

$$\text{(I)}$$

[Structure: pyranose ring with substituents: CH$_3$CNH (with S double bond), R$^1$O, OR$^1$, OR$^1$, OR$^1$, COR$^2$, OCH$_2$-ø-Y]

wherein R$^1$ is selected from the group consisting of hydrogen and acetyl; R$^2$ is selected from the group consisting of hydrogen and methyl; ø is phenyl and Y is selected from the group consisting of:

$$-\text{H}, \quad -\overset{S}{\underset{H}{\|}}\text{NCCH}_2\underset{H}{\text{N}}\text{COOC(CH}_3)_3, \quad \text{and} \quad -\overset{S}{\underset{H}{\|}}\text{NCCH}_2\text{NH}_2.$$

The invention further addresses coupling the novel compounds to a polymer carrier, forming a polyvalent viral attachment inhibitor. Polyvalent neuraminic acid derivatives have greater inhibitory activity than monovalent analogs, thus providing further reduction of the incidence of viral infection.

Another object of the invention is to provide effective processes for preparing the novel compounds.

The invention further relates to a method of treating and preventing viral infection which comprises exposing a patient to an effective amount of a monovalent or polyvalent novel neuraminic acid compound, thus effectively preventing infection or reducing the spread of infection within the body.

BRIEF DESCRIPTION OF THE DRAWINGS

The FIGURE depicts the results disclosed in Example 7.

DETAILED DESCRIPTION

The invention is illustrated with reference to the following examples, which are to be construed in a nonlimitative manner.

A. Synthesis of monomeric sialosides

EXAMPLE 1

Preparation of Methyl
(benzyl4,7,8,9-tetra-O-acetyl-3,5,-dideoxy5-thioacetamido-α-D-glycero-D-galacto
-2-nonulopyranoside)Onate A compound of the present invention in which $R^1$ is acetyl, $R^2$ is methyl, and Y is hydrogen may be prepared by a method such as the following reaction:

(II)

(III)

Specifically, a mixture of 100 mg (0.172 mmol) of a neuraminic acid having the formula (II), the synthesis of which is known in the art, and 38 mg (0.17 mmol) phosphorous pentasulfide in absolute chloroform (4 ml) were stirred under reflux for 6 h. After cooling, the mixture was diluted with 40 ml of chloroform and filtered. The filtrate was washed with saturated aqueous $NaHCO_3$ and water, dried with anhydrous $Na_2SO_4$, and evaporated to dryness. The residue was then subjected to silica gel column chromatography using toluene/ethyl acetate solvent (20–40% ethyl acetate) with an increasing amount of ethyl acetate to yield 76 mg (74% yield) amorphous compound (III): $R_f$ 0.55 (TLC on Merck Kiesegel 60 plates in toluene/ethyl acetate, 1:2); $[\alpha]_D^{20}$ +9.2° (C 0.5, chloroform). P.M.R. data (δ, $CDCl_3$, tetramethylsilane as an internal standard): 2.66, dd ($J_{3a}$ 13, $J_4$ 4, H-3e); 5.00, m (H-4, H-5); 5.28, dd ($J_5$ 8, $J_7$ 2, H-6); 5.46, dd ($J_8$ 8, J6 2, H-7); 5.47 ddd (H-8); 4.35, dd ($J_{9b}$ 12.5, $J_8$ 3, H-9a); 4.11, dd ($J_{9a}$ 12.5, $J_8$ 6, H-9b); 4.46, d, 4.85, d (J 12, H-$CH_2$Ph); 3.71, s (H-COOMe); 2.46, s (H-NC(S)Me); 7.35, m (H-Ar); 2.04, 2.07, 2.15, 2.20, 4s (H-Ac); 6.87, d ($J_5$ 10, H-NH).

EXAMPLE 2

Preparation of benzyl
3,5-dideoxy5-thioacetamido-α-D-glycero-
D-galacto-nonulopyranosidonic acid (sodium salt)

A compound of the present invention in which $R^1$ is hydrogen, $R^2$ is hydrogen, and Y is hydrogen may be prepared by a method such as the following reaction:

(III)

A solution of compound (III), 60 mg (0.1 mmol) in 4 ml 0.2N sodium methylate in methanol was allowed to stand at room temperature. After 1.5 h, 0.5 ml of 2N NaOH and 1.5 ml $H_2O$ were added and the mixture kept overnight at room temperature. Methanol was evaporated from the solution and 3 ml of $H_2O$ added. The resulting solution was passed through a KU-2 ( from U.S.S.R., may be replaced by Amberlite IR-120) column (9.5 ml, $H^+$), and the effluent collected and evaporated to dryness by rotary evaporator. The residue was resuspended in 1.5 ml $H_2O$, neutralized by dropwise addition of 0.2N NaOH and evaporated to dryness. A solution of the residue dissolved in water was applied to a Whatman Partisil 10 ODS-3 column (10×250 mm) and eluted with a 0–4% water/acetonitrile gradient. The product was detected spectrophotometrically at 200–254 nm. 35 mg of compound (IV) (80% yield) were recovered: $R_f$ 0.5 (TLC on Merck Kieselgel 60 plates in propanol/ethyl acetate/water, 2:3:1) $[\alpha]_D^{20}$ + 29° (c 0.5, water). P.M.R. data (δ$D_2O$ tetramethylsilane as an internal standard): 1.75, dd ($J_{3e}$=$J_4$ 12, H-3a); 2.82, dd ($J_{3a}$ 12, $J_4$ 5, H-3e); 3.90, ddd (H-4); 4.62, dd ($J_4$=$J_6$=10, H-5); 3.92, dd ($J_5$ 10.5, $J_7$≅2, H-6); 3.545, dd (j$_8$ 9, $J_6$≅2, H-7); 3.84, ddd (H-8); 3.87, dd ($J_{9b}$ 12, $J_8$3, H-9a); 3.64, dd ($J_{9a}$ 12, J6, H-9b); 4.79, d, 4.55, d ($J_{gem}$ 11, H-$CH_2$Ph); 7.46, m (H-Ar); 2.57, s (H-NC(S)Me) .

EXAMPLE 3

Preparation of Methyl p-(N-tert.butoxycarbonyl) thioglycylamidobenzyl(5-thioacetamido-4,7,8,9-tetra-O-acetyl-3,5,-dideoxy-α-D-glycero-D-galacto-2-nonulopyranoside)onate and methyl p-(N-tert.butoxycarbonyl) thioglycylamidobenzyl (5-acetamido4,7,8,9-tetra-O-acetyl-3,5-dideoxy-α-D-glycero-D-galacto 2-nonulopyranoside)onate A compound of the present invention in which $R^1$ is acetyl, $R^2$ is methyl, and Y is

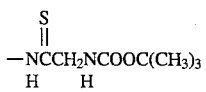

may be prepared by a method such as the following reaction:

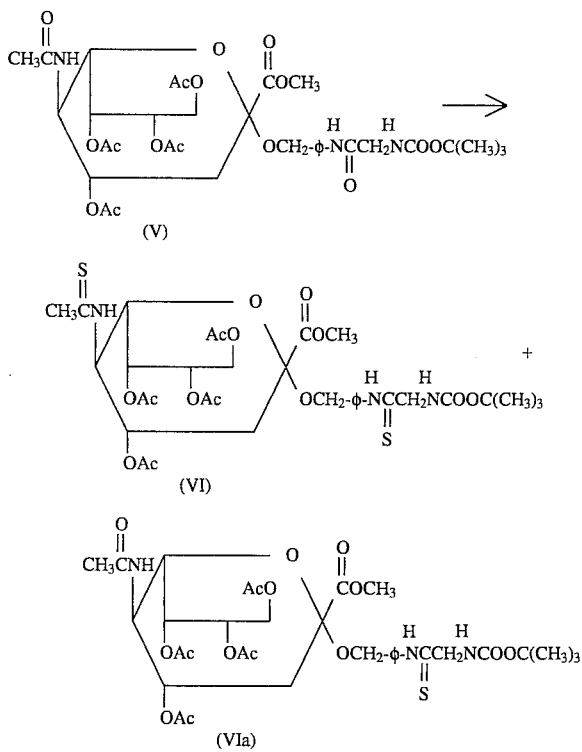

The starting material compound (V) may be synthesized according to the method of Byramova, et al., *J. Carbohydr. Chem.* 10:691–700 (1991) as follows:

Methyl (5-Acetamido-4,7,8,9-tetra-O-acetyl-3,5—dideoyxy-α-D-glycero-D galacto-nonulopyranosyl chloride)Onate Methanol (200 ml) was treated at 0° C. with acetyl chloride (1.4 ml) and added to Neu5Ac (1.36 g, 4.4 mmol), the mixture was kept overnight at room temperature, then neutralized at 0° C. with an excess of pyridine (3 ml) and concentrated. Pyridine was repeatedly added and evaporated from the residue (3×3 ml). The resulting methyl ester of Neu5Ac was finally dissolved in 20 ml of pyridine, cooled to 0° C. and treated with acetic anhydride (10 ml). After standing at room temperature overnight the mixture was treated at 0° C. with methanol (10 ml), the solvents were removed by evaporation, the residue was partitioned between chloroform (100 ml) and water (100 ml), the organic layer was washed with water (50 ml), 1N hydrochloric acid (50 ml), water, saturated sodium bicarbonate solution, water, filtered through a cotton plug and concentrated. Gradient column chromatography (Silica gel L 40–100 μm (Czechoslovakia)) using toluene with increasing amounts of ethyl acetate (–70%) gave an amorphous anomeric mixture (A. Marra, P. Sinay, Carbohydr. Res., 190, 317 (1988)) of α-($R_f$ 0.33, toluene-ethyl acetate 1:5, minor) and β-($R_f$ 0.22, major) tetraacetates, yield 1.8 g (78%). The mixture was converted (T. G. Warner, L. A. Lee, Carbohydr. Res., 176, 211 (1988)) to homogeneous chloride, which was used immediately without further purification ($R_f$ 0.46, toluene-ethyl acetate 1:5).

4-(N-tert-Butoxycarbonylglxcylamido)benzyl Alcohol

To a solution of 4-aminobenzyl alcohol (240 mg, 2 mmol) in chloroform (5 ml), N-hydroxysuccinimide ester of Boc-glycine (1 g, 3.7 mmol) and N-methylmorpholine (330 μl, 3 mmol) were added and the mixture allowed to stand 24 h at room temperature. The reaction mixture was concentrated and the N,O-diacylated product was separated from the residue using column chromatography (Silica gel L 40–100 μm (Czechoslovakia)) by elution with a gradient of toluene with an increasing amount of ethyl acetate (–25%). The product was 0-deacylated with 0.02M sodium methoxide (20 ml) in methanol for 24 h at room temperature. After neutralization with 0.02M acetic acid in toluene and concentration, the residue was subjected to column chromatography (Silica gel L 40–100 μm (Czechoslovakia)) in a toluene-ethyl acetate gradient to give the modified alcohol as an amorphous powder; yield 224 mg, (40%), $R_f$ 0.6 (chloroform-methanol 9:1), N,O-diacylated product and starting amine had $R_f$ 0.9 and 0.5, respectively. 1H NMR (CDCl$_3$) 1.41 (s, 9H, CMe$_3$), 3.84 (m near d, 3H, COCH$_2$N, OH), 4.56 (s, 2H, CH$_2$OH), 5.35 (broad s, 1H, CH$_2$NCOO), 7.21–7.40 (m, aromatic), 8.30 (broad s, 1H, PhNH).

Methyl(4-tert-Butoxycarbonylglycylamidobenzyl 5-Acetamido-4,7,8,9-tetra-O-acetyl-3,5-dideoxy-α, β-D,glycero-Dgalacto-nonulopyranoside)Onate A mixture of the modified alcohol (200 mg, 0.7 mmol), mercury cyanide (97 mg, 0.5 mmol), mercury bromide (35 mg, 0.1 mmol), molecular sieves 4A (0.5 g) and acetonitrile (5 ml) was stirred at room temperature for 2 h. A solution of the chloride described above, prepared from 200 mg (0.37 mmol) of acetate in dichloromethane (4 ml) together with an additional portion of molecular-sieves (0.4 g) was added at 0° C., and the mixture was stirred for 24 h at 4° C., then 48 h at room temperature. The reaction mixture was diluted with chloroform, washed with 1M solution of potassium iodide (30 ml), then 2M sodium chloride (30 ml), filtered through a cotton plug and concentrated to give 350 mg of the crude product. The crude product which was purified using column chromatography (Silica gel L 40–100 μm (Czechoslovakia)) by elution first with a gradient of toluene with increasing amounts of ethyl acetate (–100%), then a gradient of ethyl acetate with increasing amounts of acerone (–10%) to give a mixture of the α- and β-anomers; $R_f$ 0.20 (toluene-ethyl acetate 9:1), yield 180 mg (64%). 1H NMR (CDCl$_3$) 1.45 and 1.47 (two s, CMe$_3$), 1.82–2.12 (m, Ac), 2.55 (dd, $J_{3e,4}$=5 Hz, $J_{3e,3a}$=13 Hz, H$_{3e}$ of β), 2.63 (dd, $J_{3e,4}$=4.6 Hz, $J_{3e,3a}$=13 Hz, H$_{3e}$ of α), 3.66 and 3.75 (two s, COOMe of α and β in the ratio of 1:1), 3.98 (dd, $J_{6,7}$=2 Hz, $J_{6,5}$=10.5 Hz, H-6 of the β-anomer), 4.37 and 4.47 (two d, $J_{gem}$=12 Hz, CH$_2$Ph of the α-anomer), 4.43 and 4.52 (two d, $J_{gem}$=11.5 Hz, CH$_2$Ph of the β-anomer), 4.86 (dd, $J_{9A,\ 9B}$=12 Hz, $J_{9A,8}$=2.5 Hz, H-9A Of the β-anomer, 7.15–7.45 (m, aromatic).

The α-anomer was isolated from the resulting mixture by column chromatography (Silica gel L 40–100 (Czechoslovakia)) (chloroform/propanol-2, 3–9%) to give an amorphous compound (V), $R_f$ 0.41 (chloroform/propanol-2, 15:1, TLC on Merck Kieselgel 60 plates $[\alpha]_D^{20}$ +1° (c 0.7, chloroform). P.M.R. data ($\delta$, CDCl$_3$, tetramethylsilane as an internal standard): Neu unit 2.02 dd ($J_{3e}$=$J_4$=12.5, H-3a), 2.652 dd ($J_{3a}$ 12.5, $J_4$ 4.5, H-3e), 4.884 ddd ($J_{3e}$ 4.5, $J_5$ 10, H-4), 4.097 ddd ($J_4$ 10, H-5), 4.152 dd ($J_5$ 11, $J_7$ 2.3, H-6), 5.352 dd ($J_8$ 8, $J_6$ 2.3, H-7), 5.464 ddd (H-8), 4.335 dd ($J_{9b}$ 12.5, $J_8$ 3, H-9a), 4.112 dd ($J_8$ 6, H-9b), 5.26 d ($J_5$ 10, NH); spacer unit 4.776 and 4.404 two d (each with J 12, CH2), 8.158 broad s (ArNH), 7,483 d (J 8.8, Ar), 7.298 d (J 8.1, Ar), 5.26 near s (C(O) CH$_2$NH), 3.923 d (J 6, C (O) CH$_2$N), 3.681 s (COOMe), 2.168, 2.152, 2.05, 2.034, 1.892 five s (5 Ac), 1.489 s (CMe$_3$ ).

To synthesize compound (VI), 87 mg (0.115 mmol) of compound (V) are dissloved in 15 ml dry benzene. To this solution were added 1.5 ml pyridine and 230 mg (0.58 mmol) of Lawesson's reagent (2,4-bis (p-methoxyphenyl)-1,3-dithiadiphosphetane-2,4-disulfide; Pedersen, et al. *Bull. Soc. Chim. Belg.* 87:223 (1978)). The resultant mixture was stirred for 8 h at 80° C. After cooling, the solution was concentrated by rotary evaporation and then dried in vacuo. The residue was dissolved in 2 ml chloroform and subjected to silica gel L 40 (Czechoslovakia) column chromatography (hexane/chloroform, 2:1, with 5–14% 2-propanol).

First to elute was amorphous compound (VI). 39 mg (43% yield) of product were recovered: $R_f$ 0.68 (TLC on Merck Kieselgel 60 plates in hexane/chloroform/2-propanol, 4:2:1), $[\alpha]^{20}$–1.3° (c 3.0 chloroform) P M R data ($\delta$, CDCl$_3$, tetramethylsilane as an internal standard): Neu unit $\delta$2.04, 2.06, 2.14, and 2.19 (4s, each 3 H, 4 Ac), 2.16 (dd, $J_{3eq}$=$J_{4}$=13 Hz, H-3ax), 2.66 (dd, 1H, $J_{3ax}$ 13, $J_4$ 4 Hz, H-3eq), 5.0 (m, 2H2, H-4, H-5), 4.32 (dd, 1 H, $J_5$ 10.5 Hz, H-6), 5.27 (dd, 1 H, $J_8$ 8.5, $J_6$ 2.5 Hz, H-7), 5.45 (ddd, 1 H, H-8), 4.34 (dd, 1 H, $J_{9b}$ 12.5, $J_3$ 3 Hz, H-9a), 4.08 (dd, 1 H, $J_{9a}$ 12.5, $J_8$ 6 Hz, H-9b), 6.83 (d, 1H, $J_5$ 10.5 Hz, NH(S)), 3.71 (S, 3H, COOMe), 2.46 (s, 3H, C(S)CH$_3$), spacer unit $\delta$4.48 and 4.83 (2 d, each 1 H, J 12.5 Hz, CH$_2$Ph), 7.75 and 7.40 (2 d, each 2 H, Ph), 8.27 (broadened s, 1 H, PhNH), 4.30 (d, $J_{NH}$ 6.5 Hz, C(S)CH$_2$NH), 1.52 (s, 9 H CMe$_3$), 5.37 (broadened, C(S)CH$_2$NH).

Eluted second was 23 mg (26% yield) of amorphous compound (VIa), $R_f$ 0.45 (TLC on Merck Kieselgel 60 plates in hexane/chloroform/2-propanol, 4:2:1), $[\alpha]_D^{20}$ + 2° (c 2.0, chloroform). P.M.R. data ($\delta$, CDCl$_3$, tetramethylsilane as an internal standard): Neu unit $\delta$ 1.91 (s, 3 H, NAc), 2.05, 2.07, 2.17, 2.19 (4 s, each 3 H, 4 Ac), 2.03 (dd, 1 H, $J_{3eq}$=$J_{4}$=13 Hz. H-3ax), 2.66 (dd, 1H, $J_{3ax}$ 13, $J_4$ 4.5 Hz, H-3eq), 4.89 (m, 1 H, H-4), 4.10 (m, 1 H, H-5), 4.15 (dd, 1 H, H-6), 5.35 (dd, 1 H, $J_8$ 9, $J_6$ 2 Hz, H-7), 5.46 (ddd, 1H, H-8), 4.33 (dd, 1 H, $J_{9b}$ 12.5, $J_8$ 3 Hz, H-9a), 4.10 (dd 1 H, $J_{9a}$ 12.5, $J_8$ 6 Hz, H-9b), 3.69 (s, 3 H, COOMe), 5.19 (d 1 H, $J_5$ 10 Hz, NH); spacer unit $\delta$ 4.45 and 4.81 (2 d, each 1H, CH$_2$Ph), 7.38 and 7.73 (2 d, each 2 H, Ph), 4.30 (d 2 H, $J_{NH}$ 6.5 Hz, C (S) CH$_2$NH), 5.39 (broadened, 1 H, C(S)CH$_2$NH), 1.51 (s, 9 H, CMe$_3$).

EXAMPLE 4

Preparation of p-(N-tert-butoxycarbonyl) thioglycylamidobenzyl 3,5-dideoxy-5-Thioacetamido-$\alpha$-D-glycero-D-galactononulopyranosidonic acid (sodium salt)

A compound of the present invention in which R$^1$ is hydrogen, R$^2$ is hydrogen, and Y is

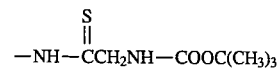

may be prepared by conventional deprotection of compound (VI) according to the following reaction:

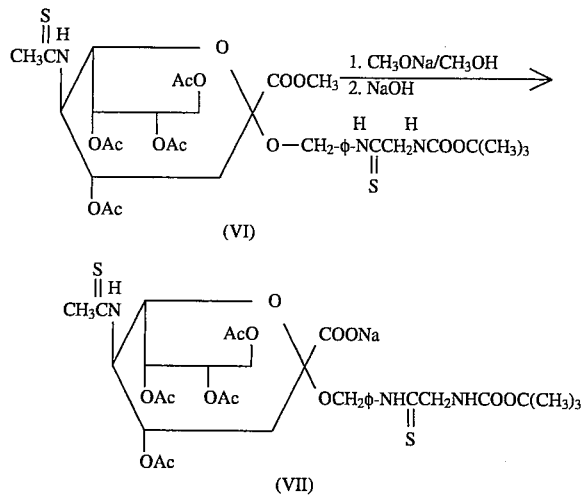

TO the solution of the compound (VI) (39.3 rag. 0.05 mmol) in dry methanol (5 ml), 2N sodium methanoxide (250 µl) was added and stored for 1 h at room temperature. Water (1 ml ) and 2N sodium methanoxide (250 ml ) were then added and stored at +10° C. for 20 h. The solution was made neutral (pH 7) by addition of acetic acid and concentrated by rotary evaporation and the residue was dried in vacuo. It was redissolved in minimum amount of 3:1 acetonitrile-water and chromatographed (methanol-water, 7:1, then 6:1) on a Cellex 410 (Bio-Rad, cat. No. 748-2231) column (20×2 cm). Appropriate fractions were collected and evaporated by rotatory evaporator to a residue, which was freeze dried to give the compound (VII) (20 rag, 64%), amorphous, $R_f$ 0.47 (TLC on Merck Kieselgel 60 plates, propanol-2/ethyl acetate/water 2:3:1), $[\alpha]_D^{20}$ +15° (c 2, water). P.M.R. data ($\delta$, D$_2$O): Neu unit 1.76 dd (near t) ($J_{3e}$ 12.5, $J_4$ 12, H-3a), 2.82 dd ($J_{3a}$ 12.5, $J_4$ 5, H-3e), 3.89 ddd ($J_5$ 10, $J_{3a}$ 12, H-4), 4.62 dd ($J_4$ 10, $J_6$ 10.5, H-5), 3.91 dd ($J_5$ 10.5, $J_7$ 1.5, H-6), 3.53 ($J_8$ 9, $J_6$ 1.5, H-7), 3.79 m (H-8), 3.85 dd ($J_{9b}$ 11.5, $J_8$ 3, H-9a), 3.65 dd ($J_{9a}$ 11.5, $J_8$ 4.5, H-9b), 2.57 s (CH$_3$CS); spacer unit 4.81 and 4.58 two d (each with J 11.5, OCH), 7.50 m (Ar), 4.27 broad s (SCCH$_2$N), 1.48 s (CMe$_3$).

EXAMPLE 5

Preparation of p-thioglycylamidobenzyl 3,5-dideoxy-5-thioacetamido-α-D-glycero-D-galacto-nonulopyranosidonic acid A compound of the present invention in which $R^1$ is hydrogen, $R^2$ is hydrogen, and Y is

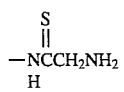

may be prepared by conventional deprotection of compound (VII), as in the following reaction:

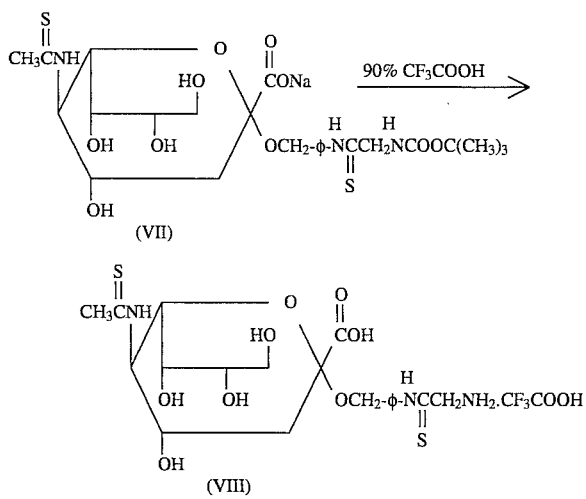

Specifically, a solution of 3.6 mg (5.7 μmol) of compound (VII) in 90% trifluoroacetic acid (1 ml) was stored at 0° C. for 1.5 h. Toluene was added and the mixture concentrated in vacuo. Addition and evaporation of toluene from the mixture was repeated several times, then the residue was dried in vacuo to give the compound (VIII), $R_f$ 0.51 (TLC on Merck Kieselgel 60 plates in propanol-2/ethyl acetate/water, 4:3:2). The compound is unstable and must be immediately used in coupling with polymer.

B. Synthesis of Polymeric Sialosides

EXAMPLE 6

Preparation of compound (VIII)/poly(acrylic acid) copoly(4-nitrophenylacrylate)conjugate 5.75 μmol of compound (VIII) were mixed with 750 μmol of solution of 7.4 mg of poly(acrylic acid) copoly(4-nitrophenylacrylate) in DMF (38.4 μmol with respect to monomeric units), 40 μl of triethylamine were then added and the mixture was kept at 20° C. for 48–60 h until monovalent sialoside depletion as judged by thin layer chromatography (TLC on Merck Kieselgel 60 plates in 2-propanol/ethyl acetate/water, 4:3:2). The resulting copolymer was further modified by the addition of 2 ml of 0.1N aqueous NaOH. 16 h later, 4-nitrophenol was removed by gel filtration on a Sephadex LH-20 column (1×25 cm; MeCN/H$_2$O, 1:1). 6.9 mg of a polymer was obtained as an amorphous solid with a total 4.6 μmol content of neuraminic acid (80% yield).

The neuraminic acid content in polymeric sialosides was assessed spectrophotometrically at 268 nm using compound (VII) as a standard ($\lambda_{max}$=268 nm, ε=18,500, water).

Preparation of a poly(acrylic acid) copoly(4-nitrophenylacrylate) conjugate of the oxygen-containing analog of compound (VIII) may be synthesized according (Matrosovich, et al., FEBS Letters 272:209–212 (1990) as follows):

3.5 μmol of the oxygen-bearing analog of compound (VIII) in 200 μl were mixed with 70 μl of 10% solution of poly(acrylic acid) copoly(4-nitrophenylacrylate) in dimethyl formamide (35 μmol with respect to monomeric units). 20 μl of triethylamine were then added and the mixture was kept at 20° C. for 48–60 hours until monovalent sialoside depletion, as judged by thin layer chromatography. The resulting copolymer was further modified by the addition of 2 ml of either 0.1N aqueous NaOH or 10% ethanolamine in dimethyl formamide. 48–72 hours later 4-nitrophenol was removed by gel filtration through a Sephadex LH-20 column (1×25 cm; MeCN/H$_2$O, 1:1). Sialoside content may be assessed spectrophotometrically at 248 nm using oxygen-bearing analog of compound (VII) as a standard ($\lambda_{max}$=248 nm, ε=17,000, water).

EXAMPLE 6a

Preparation of Compound (VIII)/poly(acrylamide) copoly(4-nitrophenylacrylate) copolymer 5.75 μmol of compound (VIII) were mixed with 750 μl of solution of 7.4 mg of poly(acrylamide) copoly(4-nitrophenylacrylate) copolymer in DMF (38.4 μmol with respect to monomeric units), 40 μl of triethylamine were then added and the mixture was kept at 20° C. for 48–60 h until monovalent sialoside depletion as judged by thin layer chromatography (TLC on Merck Kuieselgel 60 plates in 2-propanol/ethyl acetate/water, 4:3:2). The resulting copolymer was further modified by the addition of 2 ml of 25% aqueous NH$_3$. 16 h later 4-nitrophenol was removed by gel filtration on a Sephadex LH-20 column (1×25 cm; MeCN/H$_2$O, 1:1). 6.9 mg of a polymer was obtained as an amorphous solid with a total 4.6 μmol content of neuraminic acid (80% yield).

The neuraminic acid content in polymeric sialosides was assessed spectrophotometrically at 268 nm using compound (VIII) as a standard ($\lambda_{max}$=268 nm, ε=18500, water).

EXAMPLE 6b

Preparation of Compound (VIII)/poly (N-2-hydroxyethyl acrylamide) copoly (4-nitrophenylacylate)

5.75 μmol of compound (VIII) were mixed with 750 μl of solution of 7.4 mg of poly(N-2-hydroxyethyl-acrylamide) copoly(4-nitrophenylacylate) in DMF (38.4 μmol with respect to monomeric units), 40 μl of triethylamine were then added and the mixture was kept at 20° C. for 48–60 h until monovalent sialoside depletion as judged by thin layer chromatography (TLC on Merck Kuieselgel 60 plates in 2-propanol/ethyl acetate/water, 4:3:2). The resulting copolymer was further modified by the addition of 100 μl of 2-ethanolamine, 16 h later 4-nitrophenol was removed by gel filtration on a Sephadex LH-20 column (1×25 cm; MeCN/H$_2$O, 1:1). 6.9 mg of a polymer was obtained as an amorphous solid with a total 4.6 μmol content of neuraminic acid (80% yield).

The neuraminic acid content in polymeric sialosides was assessed spectrophotometrically at 268 nm using compound (VIII) as a standard ($\lambda_{max}$=268 nm, ε=18500, water).

EXAMPLE 6c

Preparation of Compound (VIII)/poly(methacrylic acid) copoly(4-nitrophenylacrylate)

5.75 μmol of compound (VIII) were mixed with 750 μl of solution of 7.8 mg of poly(methacrylic acid) copoly(4-nitrophenylacrylate) in DMF (38.4 μmol with respect to monomeric units), 40 μl of triethylamine were then added and the mixture was kept at 20° C. for 48–60 h until monovalent sialoside depletion as judged by thin layer chromatography (TLC on Merck Kuieselgel 60 plates in 2-propanol/ethyl acetate/water, 4:3:2). The resulting copolymer was further modified by the addition of 2 ml of 0.1N aqueous NaOH. 16 h later 4-nitrophenol was removed by gel filtration on a Sephadex LH-20 column (1×25 cm; MeCN/$H_2O$, 1:1). 6.9 mg of a polymer was obtained as an amorphous solid with a total 4.6 μmol content of neuraminic acid (80% yield).

The neuraminic acid content in polymeric sialosides was assessed spectrophotometrically at 268 nm using compound (VIII) as a standard ($\lambda_{max}$=268 nm, β=18500, water).

C, Neuraminidase Resistance

EXAMPLE 7

Compound (IV) was incubated at 37° C. with *Vibrio cholerae* neuraminidase (450 U/ml) in 0.1M acetate buffer, pH 5.6, containing 0.9% NaCi and 0.1% $CaCl_2$. Neuraminidase cleavage was determined on aliquots taken at intervals by TLC analysis (Merck silica gel plates in propanol/ethanol/25% aqueous ammonia, 2:2:1). Spots were developed by charring the plates with 3% $H_3PO_4$ at 150° C. and quantitated densitometrically. The results are depicted in The FIGURE (v). The acetamido analog of compound (IV), benzyl 5-acetamido3,5,-dideoxy-α-D-glycero-D-galacto-nonulopyranosidonic acid (sodium salt), was cleaved much more rapidly (⊙) than the novel compound (IV). As a control, solutions of each substrate were found to be stable in the absence enzyme for at least 23 hours.

D. Virus Affinity

EXAMPLE 8

Monomeric Sialosides

Lyophilized seed stocks of influenza viruses were obtained from the state collection of viruses at the D.I. Ivanovsky Institute of Virology, Moscow, and propagated at low multiplicity in 9–10 day old embryonated chicken eggs. Allantoic fluid was stored at −20° C., thawed, and clarified by low speed centrifugation. Partially purified virus concentrates were prepared by pelleting at 40,000 × g for 120 minutes and resuspending in 10 mMphosphate buffered saline, pH 7.2–7.4 (PBS: 140 mMNaCl), at a final concentration of 2–4 mg virus per ml.

Plastic microtiter plates were coated with bovine fetuin (Fluka, Switzerland) as follows: 0.1 ml aliquots of fetuin dissolved in PBS (10 μg/ml) were incubated in the wells of standard E.I.A. polystyrene 96-well microplates (Flow, USA) at 37° C. for 2 h. The plates were then washed with PBS containing 0.01% Tween 20 (Serra, FRG) and distilled water, and either used immediately or air dried and stored at −20 ° C.

In order to specifically adsorb viruses to the fetuin-coated wells, viruses in allantoic fluid diluted with PBS to the hemagglutinin titer of 1:50–1:200 were incubated in the fetuin-coated plates (0.1 ml/well) for 2 h at 4° C.

The binding of horseradish peroxidase-labelled fetuin (labelled according to standard periodate activation methods) by the adsorbed virions was then measured in the presence and absence of competing neuraminic acid derivatives by the following method. The plates were washed with PBS containing 0.01% Tween 20, and 0.1 ml of 0.02 μM horseradish peroxidase-labelled fetuin was added along with increasing concentrations of a neuraminic acid derivative. Following incubation for 2 h at 4° C., the plates were washed with cold PBS/Tween.

Peroxidase activity was assayed by the addition of 0.1 ml of substrate solution (0.4 mg/ml o-phenylenediamine plus 0.02% $H_2O_2$ in 50 mM sodium acetate buffer, pH 5.5) followed by incubation in the dark at room temperature for 30 minutes. 0.05 ml of a 5% solution of $H_2SO_4$ was then added and the absorbances of each well at 492 nm were determined using a Titertek Multiscan reader (Flow, Finland).

To correct for non-specific binding, a few wells were incubated with PBS in the absence of virus. Non-specific binding was found to be low ($A_{492}$ values in the range 0.05–0.2). In addition, peroxidase-fetuin conjugate binding in the absence of inhibitor was determined in order to calculate the maximum possible binding of the conjugate ($\lambda^{max}$). As a rule, these values were determined for each microtitration plate.

As a further control, binding of the peroxidase fetuin conjugate was tested after treatment of the conjugate with *Vibrio cholerae* neuraminidase. In these trials, the conjugate was found to lose its ability to bind virus, demonstrating that virus/conjugate interaction is neuraminic acid dependent.

To determine the binding affinities of the tested neuraminic acid derivatives, absorbance vs. concentration curves were plotted. Binding affinity constants were calculated according to the formula:

$$K_d = \frac{c^i \times A^i (A^{max} - A^0)}{A^{max}(A^0 - A^i)}$$

where $K_d$ is the dissociation constant of the virus/inhibitor complex; $A^0$ is the absorbance in the absence of an inhibitor; $c^i$ and $A^i$ are the concentration of inhibitor and corresponding absorbance; and $A^{max}$ is the absorbance at infinite concentration of the conjugate in the absence of inhibitor.

The results of these experiments performed with compound (IV) and its acetamido analog, benzyl 5-acetamido-3,5-dideoxy-α-D-glycero-D-galacto-nonulopyranosidonic acid (sodium salt), or compound (IX), are summarized in Table 1. The thioacetamido compound (IV) inhibits some virus strains better than its analog, which has a natural acetamido group.

TABLE 1

Working Table Illustrating Calculations of Binding by Influenza Viruses of Sialosides IV and IX

| Virus | Compound | $A^{ma}$ % | $A^0$ 0* | $A^i$ and Corresponding $-lgKd(i)$ (values in parentheses) |  |  |  |  |  | $-lgKd \pm SD$ |
|---|---|---|---|---|---|---|---|---|---|---|
| | | | | .08* | .16* | .32* | .64* | 1.28* | 2.56* | |
| USSR/90/77 | IX | 2.5 | 0.9 | — | 0.8 (3.1) | 0.7 (3.1) | — | 0.6 (2.8) | — | 3.0 ± 0.17 |
| | IV | 4.0 | 1.02 | 0.94 (3.1) | 0.84 (3.2) | 0.73 (3.2) | 0.6 (3.2) | 0.41 (3.2) | 0.23 (3.2) | 3.1 ± 0.09 |
| Chile/1/83 | IX | 1.8 | 1.00 | — | 0.9 (3.2) | 0.72 (3.4) | 0.62 (3.3) | 0.42 (3.4) | — | 3.3 ± 0.1 |
| | IV | 3.5 | 1.47 | 1.27 (3.5) | 1.14 (3.5) | 0.89 (3.5) | 0.63 (3.5) | 0.36 (3.6) | 0.25 (3.5) | 3.5 ± 0.04 |
| Taiwan/1/86 | IX | 0.95 | 0.4 | — | — | 0.36 (2.8) | 0.31 (2.9) | 0.22 (3.0) | — | 2.9 ± 0.1 |
| | IV | 2.1 | 0.75 | 0.68 (3.3) | 0.62 (3.3) | 0.55 (3.2) | 0.47 (3.1) | 0.33 (3.2) | 0.21 (3.2) | 3.2 ± 0.08 |
| X-31 | IX | 2.8 | 1.00 | — | — | 0.86 (3.1) | 0.84 (2.7) | 0.66 (2.8) | — | 2.9 ± 0.21 |
| | IV | 3.5 | 0.95 | 0.86 (3.2) | 0.72 (3.4) | 0.65 (3.3) | 0.51 (3.3) | 0.34 (3.3) | 0.24 (3.2) | 3.3 ± 0.08 |
| England/321/77 | IX | 3.6 | 1.13 | 0.49 (4.4) | 0.21 (4.6) | 0.13 (4.5) | 0.04 (4.8) | — | — | 4.5 ± 0.1 |
| | IV | 3.6 | 1.13 | 0.98 (3.4) | 0.73 (3.7) | 0.56 (3.7) | 0.37 (3.7) | 0.21 (3.7) | 0.16 (3.5) | 3.6 ± 0.13 |
| USSR/2/85 | IX | 0.9 | 0.4 | — | — | 0.32 (3.1) | 0.25 (3.3) | 0.12 (3.5) | — | 3.3 ± 0.2 |
| | IV | 1.35 | 0.33 | — | — | — | 0.28 (2.6) | 0.23 (2.6) | 0.21 (2.5) | 2.6 ± 0.06 |
| USSR/3/85 | IX | 2.0 | 1.1 | 0.5 (4.5) | 0.28 (4.6) | 0.16 (4.6) | 0.08 (4.6) | 0.06 (4.5) | — | 4.6 ± 0.05 |
| | IV | 3.2 | 1.33 | 1.05 (3.8) | 0.81 (3.8) | 0.62 (3.8) | 0.43 (3.7) | 0.32 (3.6) | 0.12 (3.8) | 3.8 ± 0.08 |
| B/Hong Kong/8/73 | IX | 1.4 | 0.60 | — | — | 0.55 (2.7) | 0.48 (2.8) | 0.32 (3.0) | — | 2.8 ± 0.15 |
| | IV | 1.4 | 0.66 | — | — | — | 0.54 (2.5) | 0.46 (2.6) | 0.32 (2.7) | 2.6 ± 0.1 |
| B/Singapore/222/79 | IX | 2.3 | 1.05 | — | 0.85 (3.4) | 0.76 (3.3) | 0.65 (3.2) | 0.39 (3.4) | — | 3.3 ± 0.1 |
| | IV | 1.75 | 0.74 | — | — | 0.56 (3.2) | 0.35 (3.5) | 0.18 (3.6) | 0.09 (3.7) | 3.5 ± 0.2 |
| B/USSR/100/83 | IX | 2.5 | 1.5 | — | 1.2 (3.6) | 1.0 (3.6) | — | 0.9 (3.1) | — | 3.4 ± 0.3 |
| | IV | 1.15 | 0.60 | — | 0.52 (3.3) | 0.40 (3.5) | 0.25 (3.7) | 0.15 (3.7) | 0.08 (3.7) | 3.6 ± 0.2 |

| Virus | Compound | $A^{ma}$ % | $A^0$ 0* | $A^i$ and Corresponding $-lgKd(i)$ (values in parentheses) |  |  |  |  |  | $-lgKd \pm SD$ |
|---|---|---|---|---|---|---|---|---|---|---|
| | | | | .05* | .10* | .20* | .40* | .80* | 1.60* | |
| Port Chalmers/1/73 | IX | 1.0 | 0.57 | 0.51 (3.7) | 0.36 (4.1) | 0.36 (3.8) | 0.33 (3.6) | 0.28 (3.5) | 0.20 (3.4) | 3.7 ± 0.3 |
| | IV | 1.0 | 0.57 | 0.55 (3.2) | 0.51 (3.4) | 0.47 (3.4) | 0.42 (3.3) | 0.40 (3.1) | 0.25 (3.2) | 3.3 ± 0.1 |
| Victoria/3/75 | IX | 1.1 | 0.73 | 0.64 (4.0) | 0.58 (4.0) | 0.45 (4.05) | 0.31 (4.1) | 0.16 (4.2) | 0.09 (4.2) | 4.1 ± 0.08 |
| | IV | 1.1 | 0.73 | 0.71 (3.4) | 0.69 (3.3) | 0.61 (3.5) | 0.56 (3.4) | 0.46 (3.4) | 0.35 (3.3) | 3.4 ± 0.08 |
| Texas/1/77 | IX | 1.2 | 1.05 | 0.77 (4.8) | 0.55 (4.9) | 0.30 (5.0) | 0.20 (4.9) | 0.09 (5.0) | 0.04 (5.1) | 5.0 ± 0.1 |
| | IV | 1.2 | 1.05 | 1.0 (3.8) | 0.9 (4.1) | 0.83 (4.0) | 0.70 (4.0) | 0.55 (3.9) | 0.35 (4.0) | 4.0 ± 0.1 |
| Philippines/2/82 | IX | 0.97 | 0.81 | 0.35 (5.2) | 0.18 (5.3) | 0.08 (5.4) | 0.05 (5.4) | 0.03 (5.3) | — | 5.3 ± 0.08 |
| | IV | 0.97 | 0.81 | 0.75 (4.0) | 0.59 (4.4) | 0.56 (4.1) | 0.43 (4.1) | 0.32 (4.1) | 0.20 (4.1) | 4.1 ± 0.14 |

*= Concentration of sialoside, $c^i$ (mM), that gives corresponding $A^i$ value in inhibition test (when $c^i = 0$, $A^i = A^0$)

EXAMPLE 9

Polymeric Sialosides

Virus binding inhibition was assayed using the fetuin binding inhibition assay as described in Example 8. The results of these experiments performed with compound (VIII)/poly(acrylic acid) conjugate and its acetamido analog/poly(acrylic acid) conjugate are summarized in Table 2.

The thioacetamido polymer conjugate inhibits some virus strains better than its analog, which has a natural acetamido group. The polymer conjugates exhibit the same character of differentiation of strains as that of the corresponding monomer. The enhancement of inhibition by the thionated polymer conjugate as compared with the thionated monomeric compound is of the same order as of the acetamido polymer conjugate as compared with its monomer.

TABLE 2

Binding by Influenza Viruses of Thionated and Non-Thionated Polymers

| Virus | Polymer Conjugate | $K_d$ (μmol) |
|---|---|---|
| USSR/3/85 | acetamido | 0.03 |
| | thionated | 0.05 |
| X-31 | acetamido | ≧40.0 |
| | thionated | 20.0 |
| X-31/63-3 | acetamido | 8.0 |
| | thionated | 2.0 |
| X-31/V9A | acetamido | 7.0 |

TABLE 2-continued

Binding by Influenza Viruses of Thionated and Non-Thionated Polymers

| Virus | Polymer Conjugate | $K_d$ (μmol) |
|---|---|---|
| | thionated | 0.8 |
| England/321/77 | acetamido | 0.13 |
| | thionated | 0.05 |
| B/Singapore/222/79 | acetamido | ≧40.0 |
| | thionated | 20.0 |
| Philippines/2/82 | acetamido | 0.1 |
| | thionated | 0.15 |

What is claimed is:

1. A composition comprising a neuraminic acid compound of the formula:

$$\begin{array}{c} S \\ \| \\ CH_3CNH \end{array} \diagdown \phantom{xxx} \diagup \begin{array}{c} O \\ \| \\ COR^2 \end{array}$$

(with $R^1O$, $OR^1$, $OR^1$, $OR^1$, $OCH_2\text{-}\phi\text{-}Y$ substituents)

wherein $R^1$ is selected from the group consisting of hydrogen and acetyl; $R^2$ is selected from the group consisting of hydrogen and methyl; and Y is selected from the group consisting of:

$$-H, \quad \underset{H}{-NCCH_2NCOOC(CH_3)_3}\overset{S}{\underset{H}{\|}}, \text{ and } \underset{H}{-NCCH_2NH_2}\overset{S}{\|}.$$

2. A composition of claim 1 which binds hemagglutinin.
3. A composition of claim 1 which binds virus particles.
4. A composition of claim 1 which binds influenza virus particles.
5. A composition of claim 1 further comprising a viral attachment inhibitor.
6. A composition of claim 1 which inhibits attachment of influenza virus.
7. A composition of claim 1 wherein said compound is substantially uncleaved by neuraminidase.
8. A composition of claim 1 wherein said compound is bound to a polymer.
9. A composition of claim 8, wherein said polymer is poly (acrylic acid).
10. A composition of claim 8 which binds hemagglutinin.
11. A composition of claim 8 which binds virus particles.
12. A composition of claim 8 which binds influenza virus particles.
13. A composition of claim 8 further comprising a viral attachment inhibitor.
14. A composition claim 8 which inhibits attachment of influenza virus to target cells.
15. A composition of claim 8 wherein said compound is substantially uncleaved by neuraminidase.
16. A method for preventing or treating viral infection comprising treating a patient with an effective amount of a composition comprising a neuraminic acid compound of the formula:

[structure diagram with $CH_3CNH$ (with S double bond), $R^1O$, $OR^1$, $OR^1$, $OR^1$, $COR^2$, $OCH_2$-$\phi$-Y]

wherein $R^1$ is selected from the group consisting of hydrogen and acetyl; $R^2$ is selected from the group consisting of hydrogen and methyl; and Y is selected from the group consisting of:

$$-H, \quad \underset{H}{-NCCH_2NCOOC(CH_3)_3}\overset{S}{\underset{H}{\|}}, \text{ and } \underset{H}{-NCCH_2NH_2}\overset{S}{\|}.$$

17. The method of claim 16 further comprising prevention or treatment of influenza virus infection.
18. A method for preventing or treating viral infection comprising treating a patient with an effective amount of a composition of claim 8.
19. The method of claim 18 further comprising prevention or treatment of influenza virus infection.

* * * * *